United States Patent
Girondin et al.

(10) Patent No.: US 10,281,438 B2
(45) Date of Patent: May 7, 2019

(54) SYSTEM AND METHOD OF DETECTING DEFECTS OF A ROLLING BEARING BY VIBRATION ANALYSIS

(71) Applicant: AIRBUS HELICOPTERS, Marignane (FR)

(72) Inventors: Victor Girondin, Aix en Provence (FR); Jean-Philippe Cassar, Ronchin (FR)

(73) Assignee: AIRBUS HELICOPTERS, Marignane (FR)

( * ) Notice: Subject to any disclaimer, the term of this patent is extended or adjusted under 35 U.S.C. 154(b) by 763 days.

(21) Appl. No.: 13/953,828

(22) Filed: Jul. 30, 2013

(65) Prior Publication Data

US 2014/0039809 A1    Feb. 6, 2014

(30) Foreign Application Priority Data

Jul. 31, 2012  (FR) ..................................... 12 02152

(51) Int. Cl.
*G01B 5/28*     (2006.01)
*G01N 29/44*    (2006.01)
(Continued)

(52) U.S. Cl.
CPC ........... *G01N 29/4463* (2013.01); *G01H 1/00* (2013.01); *G01M 13/045* (2013.01)

(58) Field of Classification Search
CPC .... G01N 29/4463; G01H 1/00; G01M 13/045
(Continued)

(56) References Cited

U.S. PATENT DOCUMENTS 5,210,704 A * 5/1993 Husseiny ............... G01H 1/003
                                                     702/34
6,695,483 B2 * 2/2004 Sakatani ................. B61F 15/20
                                                    384/448
(Continued)

FOREIGN PATENT DOCUMENTS

| EP | 0889313 A2 | 1/1999 |
| EP | 1111364 A1 | 6/2001 |
| EP | 1970691 A1 | 9/2008 |
| WO | 2010081983 A1 | 7/2010 |

OTHER PUBLICATIONS

Amit Bhende et al.; Assessment of Bearing Fault Detection Using Vibration Signal Analysis; VSRD Technical & Non-Technical Journal; VSRD-TNTJ, vol. 2(5), 2011, 249-261.
European Search report and Written Opinion; International application No. FR 1202152; dated Apr. 18, 2013.

*Primary Examiner* — Toan M Le
*Assistant Examiner* — Xiuquin Sun
(74) *Attorney, Agent, or Firm* — Brooks Kushman P.C.

(57) ABSTRACT

A method of detecting defects in a rolling bearing (10). The method includes acquiring a time-domain vibration signal $A_n$; filtering said time-domain vibration signal $A_n$; and then resolving it to obtain a deterministic time-domain vibration signal $F_n$ and a random time-domain vibration signal $G_n$. Thereafter, the time-domain vibration signals $F_n$ and $G_n$ are transformed respectively into a deterministic frequency-domain vibration signal $J_n$ and into a random frequency-domain vibration signal $K_n$, and then, for each element (11, 12, 13) and for each frequency-domain vibration signal $J_n$, $K_n$, a defect-presence frequency $\hat{\alpha}$ is determined corresponding to a maximum probability of the presence of a defect in said element (11, 12, 13) and to an associated reliability level $p(\hat{\alpha})$. An alert message indicating at least one defect in at least one element (11, 12, 13) is potentially (Continued)

delivered depending on the values of each defect-presence frequency $\hat{\alpha}$ and on each associated reliability level $p(\hat{\alpha})$.

20 Claims, 4 Drawing Sheets

(51) Int. Cl.
  *G01H 1/00* (2006.01)
  *G01M 13/045* (2019.01)
(58) Field of Classification Search
  USPC .......................................................... 702/39
  See application file for complete search history.

(56) References Cited

U.S. PATENT DOCUMENTS

| | | | |
|---|---|---|---|
| 6,847,917 B2* | 1/2005 | Bechhoefer | G01H 1/003 |
| | | | 702/182 |
| 7,136,794 B1 | 11/2006 | Bechhoefer | |
| 8,380,447 B2* | 2/2013 | Bechhoefer | G01H 1/00 |
| | | | 702/34 |
| 2010/0332186 A1 | 12/2010 | Wilson | |
| 2013/0096848 A1* | 4/2013 | Hatch | G01M 13/045 |
| | | | 702/39 |

* cited by examiner

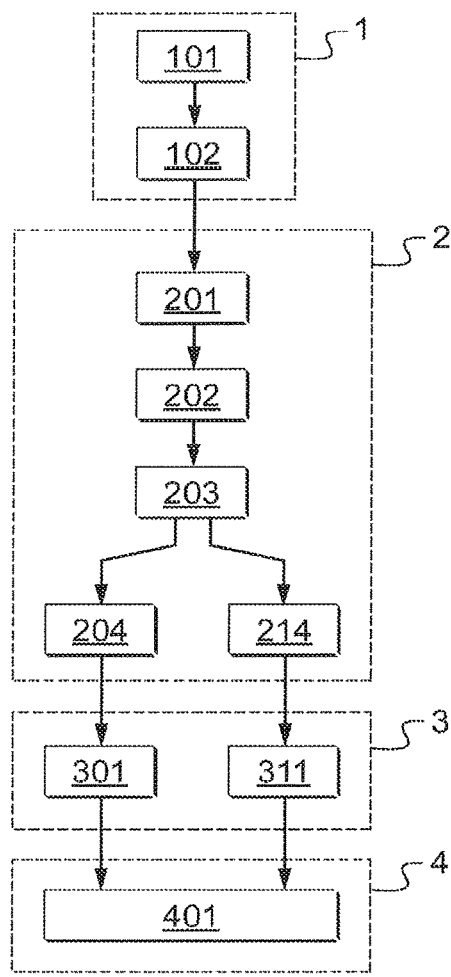
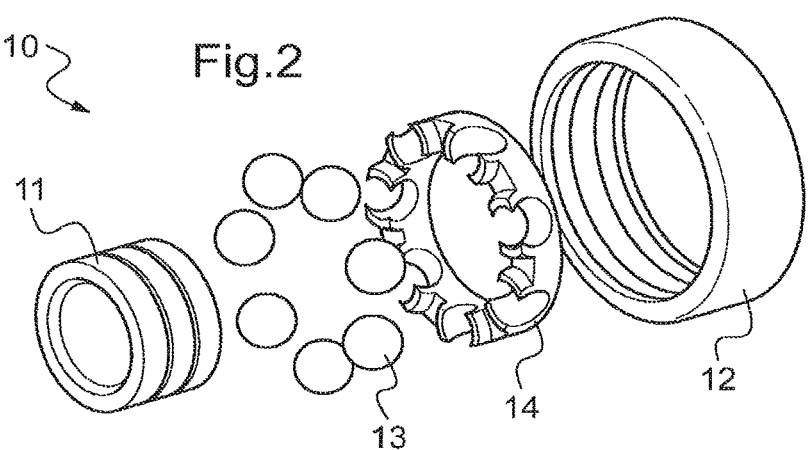

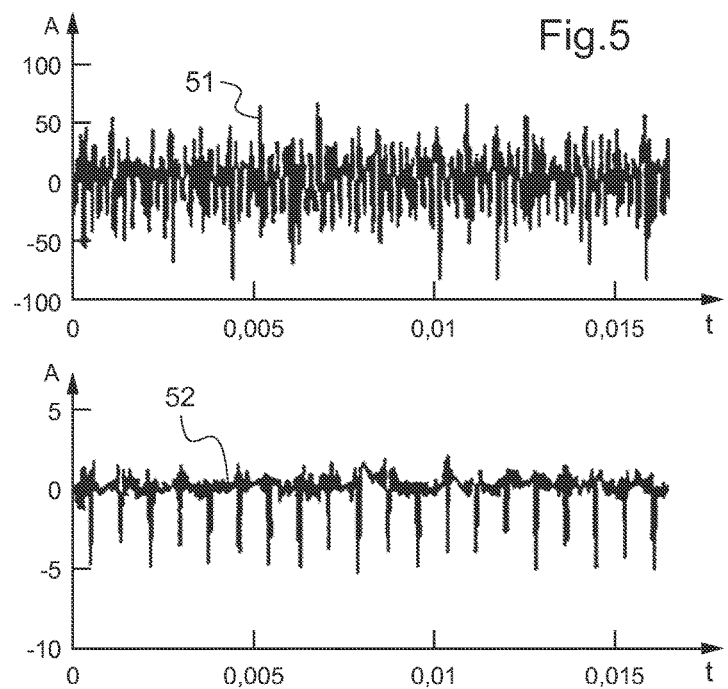
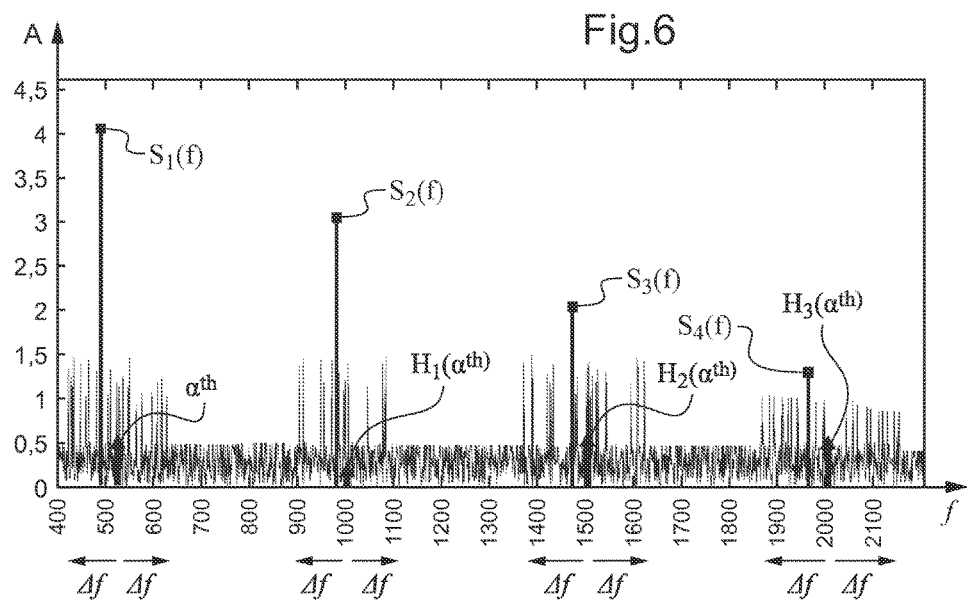

SYSTEM AND METHOD OF DETECTING DEFECTS OF A ROLLING BEARING BY VIBRATION ANALYSIS

CROSS REFERENCE TO RELATED APPLICATIONS

This application claims priority to French patent application No. FR 12 02152 filed on Jul. 31, 2012, the disclosure of which is incorporated in its entirety by reference herein.

BACKGROUND OF THE INVENTION (1) Field of the Invention

The present invention lies in the field of methods of monitoring a rolling bearing serving to provide at least some of the rotary guidance of at least one component. The invention relates more particularly to a method of detecting defects of a bearing by vibration analysis.

(2) Description of Related Art

A bearing generally acts in co-operation with at least one other bearing to provide rotary guidance for a component such as a shaft in a housing that is generally stationary, e.g. for the purpose of transmitting rotary motion and torque. Nevertheless, it is possible for the shaft to be stationary and the housing to rotate about the shaft in order to transmit rotary motion and torque. It is assumed below that it is the shaft that is rotary and the housing that is stationary.

Such a bearing conventionally comprises a plurality of elements including an inner ring, an outer ring, and a plurality of rolling bodies, such as balls or rollers. The rolling bodies may be arranged in one or two rows and they roll between the inner ring and the outer ring. The bearing may also have one or more cages for maintaining constant spacing between the rolling bodies. Nevertheless, certain bearings do not have a cage and the rolling bodies are then touching.

The inner ring of the bearing is generally secured to the shaft, with the outer ring being stationary relative to the housing in which the bearing is situated. In addition, the inner ring may form an integral portion of the shaft. Likewise, the outer ring may form an integral portion of the housing.

The shaft, which transmits the rotary motion and torque, is generally subjected to one or more kinds of stress that are transmitted at least in part to each of the bearings in the guide device. Consequently, each element of each bearing wears more or less quickly. By way of example, this wear may be in the form of degradation in the surface roughness of the inner and outer rings and also in the surface roughness or even in the shape of the rolling bodies. Such wear may also give rise to the appearance of swarf coming from the rolling bodies or from the rings.

Such wear can then generate impacts during the operation of the bearing and these lead to degradation in its operation, and consequently to degradation in the transmission of rotary motion and torque. By way of example, this degradation may go so far as to cause the bearing to seize and jam completely, thereby making it impossible to transmit the rotary motion and torque. Such impacts may also give rise to cracking in at least one of the rings and may lead to the ring breaking and thus to the bearing being destroyed.

It is then appropriate to monitor the wear of each bearing in such a guide device, and more particularly the wear of each of its elements, in order to detect early any damage to an element and thus anticipate degradation or even interruption of the transmission of rotary motion and torque by the shaft.

It is known to use a vibration signal measured in the proximity of the bearing, e.g. by an acceleration sensor, for the purpose of obtaining the vibration frequencies of each element of the bearing. A defect that is present in an element of the bearing generates vibration at a specific frequency. As a result, by filtering and isolating the various vibration frequencies emitted by the elements of a bearing while it is in operation, it is possible to deduce therefrom the presence or absence of a defect in those elements.

By way of example, document EP 0 889 313 describes a method of monitoring a mechanical transmission in a vehicle by means of acceleration sensors. After a signal has been acquired by an acceleration sensor, that time-domain signal is transformed, e.g. using a Fourier transform, into a frequency-domain signal made up of spectrum lines. Thereafter, the amplitudes of the spectrum lines are modified as a function of their frequencies and of reference frequencies and also in application of a predetermined relationship. Finally, a sixth-order moment of the sequence of the resulting spectrum lines is compared with a predetermined threshold in order to define whether there is a defect within the transmission of the vehicle.

In addition, document EP 1 111 364 describes a method of detecting damage to engine parts, such as ball bearings. Such a method enables monitoring to be continuous and enables such damage to be detected early by comparing a vibration signal obtained by at least one acceleration sensor on the system with signals previously recorded during a preliminary stage on the same system when it was without defect and on the same system including various possible defects. During acquisition of the vibration signal, it is initially verified that the speed of rotation of the engine has remained stable in order to limit the presence of noise in the vibration signal, and then the time-domain vibration signal is transformed into a frequency-domain signal, while eliminating fundamental frequencies specific to the engine.

Thereafter, coherence is calculated between the frequency-domain signal and the same frequency-domain signal shifted to the frequency that corresponds to a defect and that was found during the preliminary stage. Analyzing the coherence peaks as obtained in that way with predetermined thresholds makes it possible to determine whether or not a defect is present on one or more parts of the engine.

Document EP 1 970 691 describes a method of detecting the wear of a rolling bearing in a turbine engine. Firstly a vibration signal is acquired during a stage of low-speed and renewable rotation of the engine in order to obtain a reliable signal that is little affected by noise. After transforming this time-domain vibration signal into a frequency-domain signal, the mean of the amplitude of the spectrum lines is calculated, and then a ratio is calculated between amplitude peaks close to frequencies that are multiples of a theoretical frequency corresponding to a defect and the amplitude from a bearing having no defect. Finally, this ratio is compared with a predetermined threshold that serves to define whether or not a defect is present.

In addition, document WO 2010/081983 describes a method and a system for monitoring a turbine engine that serves to reveal a defect or abnormal operation of the engine. After acquiring a vibration signal and transforming it into a frequency-domain signal, the frequency-domain vibration signal is compared with various signals that have previously been obtained and that correspond to the same type of engine when it has a defect or its operation is abnormal. After the comparison, a message might possibly be issued indicating the component that has a defect or operation that is abnormal.

In addition, document U.S. Pat. No. 7,136,794 describes a method of estimating one or more condition indicators for use in determining a health indicator about the operation of a component. That method is for a component of a mechanical system such as gearing and/or ball bearings, the condition indicators and a health indicator serving to detect defects in the component. The condition indicators may be determined from data coming from sensors of the component or of the system and also from configuration data for the component or the system.

Document US 2010/0332186 describes a method of determining the time interval between periodic events disturbing a signal. A probability of this time interval is a function of the probabilities of those events occurring, which probabilities are themselves obtained from values of the signal.

Finally, the publication "Assessment of bearing fault detection using vibration signal analysis" published in VSRD Technical and Non-Technical Journal of 2011 describes various vibration analysis techniques applied to monitoring ball bearings, in particular by analyzing the amplitudes and the frequencies of vibration signals, e.g. acquired by accelerometers. The vibration signals may be analyzed in the time domain or in the frequency domain.

The drawbacks that can be found in those various methods lie mainly in the difficulty of isolating the frequencies that relate to defects in the elements of the bearing, and also to the level of reliability that can be given to those frequencies.

The measured signal does indeed contain the frequencies of the vibrations emitted by the bearing and by its elements, but it also contains interfering vibrations that pollute the measured signal and that prevent the vibration frequencies that reveal the looked-for defects from being isolated effectively. Those interfering vibrations are emitted mainly by other components in the proximity of the bearing, such as the shaft and the components of the guide device. Those interfering vibrations may be generated firstly by the rotation of the shaft and the torque it is transmitting and also by the stresses to which it is subjected, and secondly by external elements, such as the explosions in an engine to which the shaft is connected or the vibration of a vehicle in which the guide device is installed.

The difficulty that is encountered for isolating the frequencies of the defects of bearing elements makes it difficult to estimate a reliability level for such defect detection. Furthermore, the variations in the speed of rotation of the shaft have a direct effect on the vibration frequencies of the bearing and of its elements, and consequently on such a level of reliability.

Finally, certain systems that use bearings require information processing to take place in a very short period of time and a decision to be made very quickly as to the presence or the absence of a defect, e.g. within a time of about one minute. Such a decision must for example be taken between two stops of a system or during a period in which the system is operating at a speed of rotation that is low and stable. In contrast, certain methods require successive measurements in order to detect variation in the behavior of elements of a bearing that might correspond to a degradation of such an element, and as a result they are not suitable for such systems.

BRIEF SUMMARY OF THE INVENTION

An object of the present invention is to propose a method that makes it possible to mitigate the above-mentioned drawbacks so as to detect defects in elements of a rolling bearing in a manner that is reliable, early, and fast, by analyzing a vibration signal.

The bearing generally forms part of a device for guiding a component in rotation, e.g. a shaft, with the guide device itself being incorporated in a system. By way of example, the system may be an engine that transmits rotary motion and torque via the shaft. The system includes at least one acceleration sensor positioned in the proximity of the bearing in order to pick up the vibration emitted by the bearing and more particularly by its elements.

It is known that for each element of a bearing, a defect is manifested mainly by the appearance of one or more impacts during operation, thereby generating at least one energy peak at a particular frequency of vibration, and also at frequencies that are multiples of this particular frequency of vibration, which multiple frequencies are referred to as harmonics. This particular frequency of vibration can be calculated theoretically and is referred to herein as the "theoretical fundamental frequency $\alpha^{th}$".

In the invention, a method of detecting defects in a bearing comprises four steps.

Firstly, during a preliminary step, for each element of the bearing, at least one theoretical fundamental frequency $\alpha^{th}$ is determined that corresponds to a defect of that element, and then a frequency dispersion $\Delta f$ around that theoretical fundamental frequency $\alpha^{th}$ is determined together with a theoretical fundamental probability $p^{prior}(f)$ that each frequency f in the range:

$$[\alpha^{th}-\Delta f, \alpha^{th}+\Delta f]$$

does indeed correspond to this defect in this element.

Thereafter, during a preprocessing step, a time-domain vibration signal A is acquired over a predetermined acquisition time from the acceleration sensor positioned in the proximity of the bearing. This time-domain vibration signal A comprises in known manner a sequence of N digital samples $A_1, A_2, \ldots, A_n, \ldots, A_N$ where n is the order number of each sample in the signal and varies over the range 1 to N. Below, this time-domain vibration signal A is written $A_n$, and more generally any vibration signal X is written $X_n$. This time-domain vibration signal $A_n$ is transformed during this preprocessing step in order to be analyzed.

Thereafter, in an analysis step, for each element of the bearing, at least one defect-presence frequency $\hat{\alpha}$ and an associated reliability level $p(\hat{\alpha})$ are determined, where each defect-presence frequency $\hat{\alpha}$ lies in a range:

$$[\alpha^{th}-\Delta f, \alpha^{th}+\Delta f]$$

with $\alpha^{th}$ being the theoretical fundamental frequency of the detected defect.

Finally, during a diagnosis step, an alert message might possibly be delivered indicating at least one defect in at least one element of the bearing as a function of the values of each defect-presence frequency $\hat{\alpha}$ and each associated reliability level $p(\hat{\alpha})$.

Firstly, this method is a method that is absolute in the sense that a single acquisition suffices to determine whether or not there is a defect in an element of the bearing. Unlike other methods that are based for example on variation in measurements over various operating cycles of the bearing, the method of the invention performs a single preprocessing step, a single analysis step, and a single diagnosis step. As a result, the time needed for making a decision about the presence of a defect is short, and thus makes it possible to act during a short stoppage period of a system or during a period in which its speed of rotation is stable.

As a result, the predetermined acquisition time for the signal emitted by the acceleration sensor can be quite long, in particular in order to contain sufficient information about the elements of the bearing without that degrading the performance of the method of the invention. This predetermined acquisition time depends on the observed defect frequency. By way of example, it may be about fifty theoretical periods $T^{th}$ of a vibration signal corresponding to a defect in a bearing, i.e. the reciprocal of a theoretical fundamental frequency $\alpha^{th}$, such that $T^{th}=1/\alpha^{th}$. This predetermined acquisition time may have a duration of about three seconds.

During the preliminary step, it is possible, for each potential defect of each element of the bearing, to determine in conventional manner at least one theoretical fundamental frequency $\alpha^{th}$ for the defect, this theoretical fundamental frequency $\alpha^{th}$ depending mainly on the shape of the element and on its speed of rotation.

Nevertheless, there may be a difference between the theoretical fundamental frequency $\alpha^{th}$ and the real frequency $\hat{\alpha}$ for the presence of this defect, e.g. as a function of operating conditions of the bearing, such as the stresses to which the bearing is subjected that might deform its elements, or indeed such as dimensional dispersions between such elements. Such a difference can greatly disturb detecting the defect. Advantageously, a frequency readjustment method is then used by the method of the invention in order to find this real frequency $\hat{\alpha}$ for the presence of this defect in each element. In the description below, this real frequency $\hat{\alpha}$ is designated by the expression "defect-presence frequency $\hat{\alpha}$".

This defect-presence frequency $\hat{\alpha}$ thus corresponds to a vibration frequency that is characteristic of a defect present in an element of the bearing.

In the context of this frequency readjustment method, it is initially assumed that the defect-presence frequency $\hat{\alpha}$ may depart from the theoretical fundamental frequency $\alpha^{th}$ by no more than a value $\Delta f$, which is referred to as the frequency dispersion. Still during this preliminary step, it is then possible to estimate a theoretical fundamental probability $p^{prior}(f)$ for each frequency f situated in the dispersion range:

$$[\alpha^{th}-\Delta f, \alpha^{th}+\Delta f]$$

that said frequency f is the defect-presence frequency $\hat{\alpha}$. This theoretical fundamental probability $p^{prior}(f)$, which is determined before acquiring the vibration signal from elements that are to be monitored, may also be referred to as the "a priori probability". Its value lies in the range 0 to 1.

The frequency dispersion $\Delta f$ may for example be obtained by experiment, e.g. after performing statistical calculations on the basis of measurements made on elements having the defect. This theoretical fundamental probability $p^{prior}(f)$ may then follow a normal relationship with a mean $\alpha^{th}$ and a standard deviation $\Delta f$, also known as a Gaussian curve. This theoretical fundamental probability $p^{prior}(f)$ may also follow a relationship based on a large number of reference states of a degraded bearing.

This preliminary step may be performed on a single occasion prior to running the system containing the bearing monitored by the method of the invention and it is not performed on each cycle of the method. Nevertheless, it is possible for this preliminary step to be updated in order to add new reference states resulting from measurements taken by the method on bearings presenting defects, thus making it possible in particular to refine the relationships for determining the theoretical fundamental probability $p^{prior}(f)$.

Thereafter, the following steps may be performed in order to perform monitoring proper of the bearing, and more particularly of its elements.

During the preprocessing step, and during the predetermined acquisition time, the time-domain vibration signal $A_n$ comprising N samples is initially acquired.

This time-domain vibration signal $A_n$ contains the vibration signal from each element of the bearing, and also a multitude of interfering vibration signals, e.g. emitted by all of the other components of the system containing the bearing. It is then appropriate to filter the time-domain vibration signal $A_n$ in order to eliminate those interfering vibration signals as well as possible. This produces a filtered time-domain vibration signal $A'_n$ that contains essentially the vibration signal from each of the elements of the bearing.

Firstly, the speed of rotation of the shaft with which the bearing is connected may vary during the predetermined acquisition time for the time-domain vibration signal $A_n$, and may consequently disturb the time-domain vibration signal $A_n$. However it is possible to correct this time-domain vibration signal $A_n$ by using the instantaneous speed of rotation of the shaft, which speed can be measured by suitable measurement means. This known method thus makes it possible to synchronize the time-domain vibration signal $A_n$ with the instantaneous speed of rotation of the shaft, thereby eliminating this particular disturbance.

Thereafter, in order to obtain a time-domain vibration signal $A_n$ capable of detecting a defect in an element of the bearing in reliable and effective manner, it is necessary to eliminate the interfering vibratory components that it contains. These interfering vibratory components may come firstly from other components of the system containing the bearing, such as gears and an engine, and secondly from potentially unknown disturbances external to the system.

It is then appropriate to process these two sources of interfering vibratory components. The other components of the system have speeds that are known and often different from the speeds of the elements of the monitored bearing. Furthermore, their configurations and their positions in the system are known, and consequently the frequencies of the vibrations they generate can also be known. It is thus possible to eliminate these frequencies from the time-domain vibration signal $A_n$ in order to eliminate the interfering vibratory components from those other components of the system.

In contrast, interfering frequencies from disturbances external to the system are unknown. However, the theoretical fundamental frequency $\alpha^{th}$ of each looked-for defect is known, as is the frequency dispersion $\Delta f$ associated with each theoretical fundamental frequency $\alpha^{th}$. It can then be assumed that the frequencies present in the time-domain vibration signal $A_n$ that are offset from each theoretical fundamental frequency $\alpha^{th}$ and its harmonics by a value greater than the associated frequency dispersion $\Delta f$ must correspond to disturbances external to the system and should therefore be eliminated.

Furthermore, in order to ensure that this elimination of interfering vibratory components is effective, it is advantageous to process a signal in the frequency domain rather than a signal in the time domain. A time-domain signal represents the variation in the amplitude or in the intensity of a signal as a function of time and therefore does not make it easy to reveal the various frequencies that make it up. Conversely, a signal in the frequency domain represents the variation in the amplitude or in the intensity of a signal as a function of frequency, and is thus made up of frequency spectrum lines.

From such a frequency-domain signal it is thus easy to view and to eliminate the frequencies of the interfering vibratory components.

A known method of transforming a time-domain signal into a frequency-domain signal is to use the Fourier transform. Conversely, the inverse Fourier transform is used to transform a frequency-domain signal into a time-domain signal.

In order to eliminate the interfering vibratory components from the time-domain vibration signal $A_n$, the following substeps are performed:

transforming the time-domain vibration signal $A_n$ into a frequency-domain vibration signal $B_n$;

eliminating from the frequency-domain vibration signal $B_n$ the frequencies of mechanical vibrations coming from the components of the system outside the bearing at mechanical vibration frequencies that are known;

eliminating from the frequency-domain vibration signal $B_n$ frequencies that are offset from each theoretical fundamental frequency $\alpha^{th}$ of each of the elements and from its harmonics by a value that is greater than the associated frequency dispersion $\Delta f$, thereby obtaining the frequency-domain vibration signal $B'_n$ as modified in this way; and transforming the frequency-domain vibration signal $B'_n$ as modified in this way in order to obtain a filtered time-domain vibration signal $A'_n$.

Thereafter, after filtering this time-domain vibration signal $A_n$, the filtered signal $A'_n$ is resolved into two signals, a deterministic time-domain vibration signal $D_n$ and a random time-domain vibration signal $E_n$.

Advantageously, resolving in this way facilitates subsequent analysis and detection of a defect, in particular by revealing information about the nature of the defect during diagnosis. The deterministic signal and the random signal, both present in the signal $A_n$, represent noise relative to each other. Thus, the final decision is less accurate when those two signals remain mixed together. Furthermore, if the random signal is not extracted and processed separately, a defect contained solely in the random signal cannot be isolated and consequently cannot be detected. Resolving these two signals thus presents two advantages, firstly it improves the robustness of the processing of the deterministic signal by eliminating the noise generated by the random signal, and secondly it enables the random signal to be processed appropriately.

In contrast, conserving the deterministic time-domain vibration signal $D_n$ and a random time-domain vibration signal $E_n$ mixed together in a single time-domain signal $A'_n$ can harm decision making concerning the presence or absence of defects, and in particular a defect that is present solely in the random signal may be missed.

By definition, a signal is deterministic, or predictable, if all of its future values are predictable from its past values. For example, a periodic signal is predictable since it suffices to know that signal over a single period.

It is thus possible to write this deterministic time-domain vibration signal D in the form:

$$D_n = a_1 \cdot A'_{n-1} + a_2 \cdot A'_{n-2} + \ldots + a_{n-1} \cdot A'_1$$

where $a_1, a_2, \ldots, a_{n-1}$ are coefficients associated with respective samples of the filtered time-domain vibration signal $A'_n$. The random time-domain vibration signal $E_n$ is then the difference between the filtered time-domain vibration signal $A'_n$ and the deterministic time-domain vibration signal $D_n$, such that:

$$E_n = A'_n - D_n$$

Advantageously, it is possible to reduce the number of past samples that are used for determining the deterministic time-domain vibration signal $D_n$ so as to obtain a compromise between the speed of calculation and the accuracy of this deterministic time-domain vibration signal $D_n$. It is possible to write:

$$D_n = a_1 \cdot A'_{n-1} + a_2 \cdot A'_{n-2} + \ldots + a_r \cdot A'_{n-r}$$

where $a_1, a_2, \ldots, a_r$ are coefficients associated respectively with the samples of the filtered time-domain vibration signal $A'_n$ and where r is the number of samples used for the calculation. The number of samples r is less than n. The coefficients $a_1, a_2, \ldots, a_r$ are then determined by the known least-squares method, i.e. by minimizing the sum:

$$\Sigma_{n=N-r}^{N} (A'_n - D_n)^2$$

The deterministic time-domain vibration signal $D_n$ and the random time-domain vibration signal $E_n$ as obtained in this way can be used during the analysis step in order to determine each defect-presence frequency $\hat{\alpha}$ and each associated reliability level $p(\hat{\alpha})$.

However, in order to improve the analysis of the vibration signals and finalize their transformation, it is also possible to improve the impulsiveness of the deterministic time-domain vibration signal $D_n$ and of the random time-domain vibration signal $E_n$ during this processing step. This transformation reveals more clearly information that is useful in analyzing the frequencies of these signals, and consequently in detecting a defect, if any, in an element of the bearing.

A defect in a bearing gives rise in particular to repeated impacts that lead to peaks of large amplitude in the time-domain vibration signal $A_n$, with these peaks occurring at at least one particular frequency and its harmonics. The presence of these large-amplitude peaks is a characteristic known as impulsiveness. The presence of such peaks in the time-domain vibration signal $A_n$ can be made clearer, and consequently the presence of such impacts in the bearing can be made clearer, if amplification is applied essentially to these peaks. For example, it is possible to increase the impulsiveness of a signal by means of a self-adaptive filter, i.e. a filter having coefficients that adapt automatically to the signal.

The impulsiveness of a time-domain vibration signal is mathematically quantified by an indicator that is known to the person skilled in the art as the "Kurtosis" indicator or indeed the "normalized statistical fourth cumulant".

In the present method, since the time-domain vibration signal $A_n$ has already been filtered and resolved into a deterministic time-domain vibration signal $D_n$ and a random time-domain vibration signal $E_n$, the impulsivity of these two (deterministic and random) signals $D_n$ and $E_n$ is therefore improved in order to obtain an improved deterministic time-domain vibration signal $F_n$ and an improved random time-domain vibration signal $G_n$.

As above, the improved deterministic time-domain vibration signal $F_n$ is a linear combination of earlier samples of the deterministic time-domain vibration signal $D_n$ such that:

$$F_n = b_1 \cdot D_{n-1} + b_2 \cdot D_{n-2} + \ldots + b_p \cdot D_{n-p}$$

where p is the number of samples used for calculating the improved deterministic time-domain vibration signal $F_n$ and where the coefficients $b_1, b_2, \ldots, b_p$ are determined so as to maximize the Kurtosis indicator, quantifying the impulsiveness of the improved deterministic time-domain vibration signal $F_n$. This Kurtosis indicator is given by the following formula:

$$\text{Kurtosis}(F_n) = \frac{1}{N} \frac{\sum_{n=1}^{N} \left(F_n - \frac{1}{N}\sum_{n=1}^{N} F_n\right)^4}{\sigma_F^4}$$

where $\sigma_F$ is the standard deviation of the improved deterministic vibration signal $F_n$. Once more, the number of samples p may be less than n so as to reduce the number of past samples that are used for determining the improved deterministic time-domain vibration signal $F_n$ in order to obtain a compromise between the speed and the accuracy of the calculation.

In order to obtain the improved random time-domain vibration signal $G_n$, it is necessary to perform an intermediate operation. It is necessary initially to apply a specific transformation to the random time-domain vibration signal $E_n$ in order to obtain an intermediate signal $E'_n$ such that:

$$E'_n = |E_n + i \times H(E_n)|^2$$

where H is the Hilbert transform and i is the imaginary number such that $i^2 = -1$. Thereafter, the improved random time-domain vibration signal $G_n$ is determined as a linear combination of earlier samples of the intermediate signal $E'_n$, such that:

$$G_n = c_1 \cdot E'_{n-1} + c_2 \cdot E'_{n-2} + \ldots + c_q \cdot E'_{n-q}$$

where q is the number of samples used for calculating the improved deterministic time-domain vibration signal $G_n$ and is less than n. The coefficients $c_1, c_2, \ldots, c_4$ are determined so as to maximize the Kurtosis indicator. This Kurtosis indicator is given by the following formula:

$$\text{Kurtosis}(G_n) = \frac{1}{N} \frac{\sum_{n=1}^{N} \left(G_n - \frac{1}{N}\sum_{n=1}^{N} G_n\right)^4}{\sigma_G^4}$$

where $\sigma_G$ is the standard deviation of the improved random time-domain vibration signal $G_n$.

Thus, from the time-domain vibration signal $A_n$ containing interfering information, an improved deterministic time-domain vibration signal $F_n$ and an improved random time-domain vibration signal $G_n$ are obtained that have been filtered and in which the amplitudes associated with the frequencies that are representative of defects have been amplified. These improved time-domain vibration signals $F_n$ and $G_n$ are thus ready to be analyzed.

Thereafter, during the analysis step, for each deterministic time-domain vibration signal and for each random time-domain vibration signal there are determined respectively at least one defect-presence frequency $\hat{\alpha}$ corresponding to a maximum probability for the defect-presence frequency for each element of the bearing and also with an associated reliability level $p(\hat{\alpha})$.

In order to determine each defect-presence frequency $\hat{\alpha}$, it is more advantageous to process a frequency-domain signal than a time-domain signal. As a result, each deterministic and random time-domain vibration signal is transformed respectively into a deterministic frequency-domain vibration signal $J_n$ and a random frequency-domain vibration signal $K_n$ so as to obtain spectrum lines of amplitude $S(f)$ for each frequency-domain vibration signal $J_n$, $K_n$ and for each element of the bearing. By way of example, this transformation is performed by using the Fourier transform.

Thereafter, for each element of the bearing, for each frequency-domain vibration signal $J_n$, $K_n$, and for each frequency f in the range:

$$[\alpha^{th} - \Delta f, \alpha^{th} + \Delta f]$$

an experimental probability $p^{post}(f)$ is calculated for the presence of a defect in the element.

This experimental probability $p^{post}(f)$ that is determined from the time-domain vibration signal $A_n$ may also be referred to as the "a posteriori probability". Its value lies in the range 0 to 1.

Finally, for each element and for each frequency-domain vibration signal $J_n$, $K_n$, it is possible to determine firstly the defect-presence frequency $\hat{\alpha}$ at which the experimental probability $p^{post}(f)$ is at a maximum when f runs along the range:

$$[\alpha^{th} - \Delta f, \alpha^{th} + \Delta f]$$

and secondly the associated reliability level $p(\hat{\alpha})$, which is equal to this maximum experimental probability $p^{post}(f)$.

The experimental probability $p^{post}(f)$ may be calculated using the formula:

$$p^{post}(f) = \frac{p^{prior}(f) \times \prod_{m=1}^{M} S_m(f)}{\int_{v=\alpha^{th}+\Delta f}^{\alpha^{th}+\Delta f} \left[p^{prior}(v) \times \prod_{m=1}^{M} S_m(v)\right] \cdot dv}$$

where $p^{prior}(f)$ is the theoretical fundamental probability of the frequency f in the range:

$$[\alpha^{th} - \Delta f, \alpha^{th} + \Delta f]$$

$\Delta f$ is the frequency dispersion around the theoretical fundamental frequency $\alpha^{th}$, $S_m(f)$ is the amplitude of the spectrum line for the frequency $m \times f$, such that $S_m(f) = S(m \times f)$, and M is the number of harmonics of f taken into account in the formula.

In a first variant of the invention, the experimental probability $p^{post}(f)$ may be calculated using the formula:

$$p^{post}(f) = \frac{p^{prior}(f) + \sum_{m=1}^{M} S_m(f)}{\int_{v=\alpha^{th}+\Delta f}^{\alpha^{th}+\Delta f} \left[p^{prior}(v) + \prod_{m=1}^{M} S_m(v)\right] \cdot dv}$$

In a second variant of the invention, the experimental probability $p^{post}(f)$ may be calculated using the formula:

$$p^{post}(f) = \frac{\min_{m=1 \text{ to } M} p^{prior}(f) \times S_m(f)}{\int_{v=\alpha^{th}+\Delta f}^{\alpha^{th}+\Delta f} \min_{m=1 \text{ to } M} \left[p^{prior}(v) \times S_m(v)\right] \cdot dv}$$

Finally, during the diagnosis step, an alert message might possibly be delivered indicating at least one defect in at least one element of the bearing as a function of the values of each defect-presence frequency $\hat{\alpha}$ and of each associated reliability level $p(\hat{\alpha})$.

Advantageously, this alert message makes it possible to identify the defect that has been detected and the element that is concerned, each defect-presence frequency $\hat{\alpha}$ being specific to a given defect and to a particular element of the bearing.

For this purpose and for each element of the bearing, the information about both the deterministic and the random time-domain vibration signals obtained during the preprocessing step, i.e. each defect-presence frequency $\hat{\alpha}$ and each associated reliability level $p(\hat{\alpha})$ are brought together in order to be combined.

This diagnosis is an operation making it possible to decide whether or not to trigger an alert indicating a defect in at least one element of the bearing on the basis of the analysis of both defect-presence frequencies $\hat{\alpha}$ and their associated reliability levels $p(\hat{\alpha})$. Several situations can be distinguished.

For example, for a given defect in an element of the bearing, if both defect-presence frequencies $\hat{\alpha}$ in the deterministic time-domain vibration signal and in the random time-domain vibration signal are far apart, then at least three circumstances can be distinguished:

either at least one of the two defect-presence frequencies $\hat{\alpha}$ has a reliability level $p(\hat{\alpha})$ that is small compared to the other, and then account is taken only of the frequency having the larger reliability level $p(\hat{\alpha})$ in order possibly to trigger an alert message corresponding to that defect-presence frequency $\hat{\alpha}$;

or both of the defect-presence frequencies $\hat{\alpha}$ have high levels of reliability $p(\hat{\alpha})$, so an alert message is potentially triggered depending on a maintenance strategy decided by the user, e.g. by combining the two reliability levels $p(\hat{\alpha})$. It is possible to use the "mini-max" strategy, which consists in minimizing the maximum loss, i.e. assuming a worst-case scenario. In the context of the invention, this strategy consists in taking the greater of the reliability levels $p(\hat{\alpha})$, i.e. expecting the worst of the possible defects;

or else both of the reliability levels $p(\hat{\alpha})$ are low and no alert message is triggered.

Otherwise, when both defect-presence frequencies $\hat{\alpha}$ are close together, the two reliability levels $p(\hat{\alpha})$ are combined. For example, such a combination may give as its result the greater value or the average of the reliability levels $p(\hat{\alpha})$.

Under all circumstances, the single reliability level $p(\hat{\alpha})$ that is used or the combination of the two reliability levels $p(\hat{\alpha})$ is compared with the alert threshold corresponding to this given defect of an element of the bearing and an alert message corresponding to the presence of this given defect is delivered if the alert threshold is exceeded.

The alert thresholds for each defect and for each element are determined by the person skilled in the art as a function of a large number of reference states for a sound bearing and for a degraded bearing. The alert thresholds may also take account of desired rates of non-detection and of false alarms.

Putting the method of the invention into place requires knowledge of numerous reference states of a sound bearing and of a degraded bearing in order to cover a large number of parameters such as the static and dynamic loading of the bearing, various speeds of rotation, and various operating temperatures.

BRIEF DESCRIPTION OF THE SEVERAL VIEWS OF THE DRAWINGS

The invention and its advantages appear in greater detail from the context of the following description of implementations given by way of illustration and with reference to the accompanying figures, in which:

FIG. 1 is a diagram summarizing the method of the invention;

FIG. 2 is an exploded view of a ball bearing;

FIGS. 4, 5, and 6 are graphs plotting curves representing various vibration signals during the method of the invention.

Elements present in more than one of the figures are given the same references in each of them.

DETAILED DESCRIPTION OF THE INVENTION

FIG. 1 is a diagram summarizing the method of the invention that takes place in four main steps performed by a processor, each of these main steps comprising one or more substeps. The method is a method of detecting defects in a rolling bearing 10 by analyzing vibration.

Figure 7:
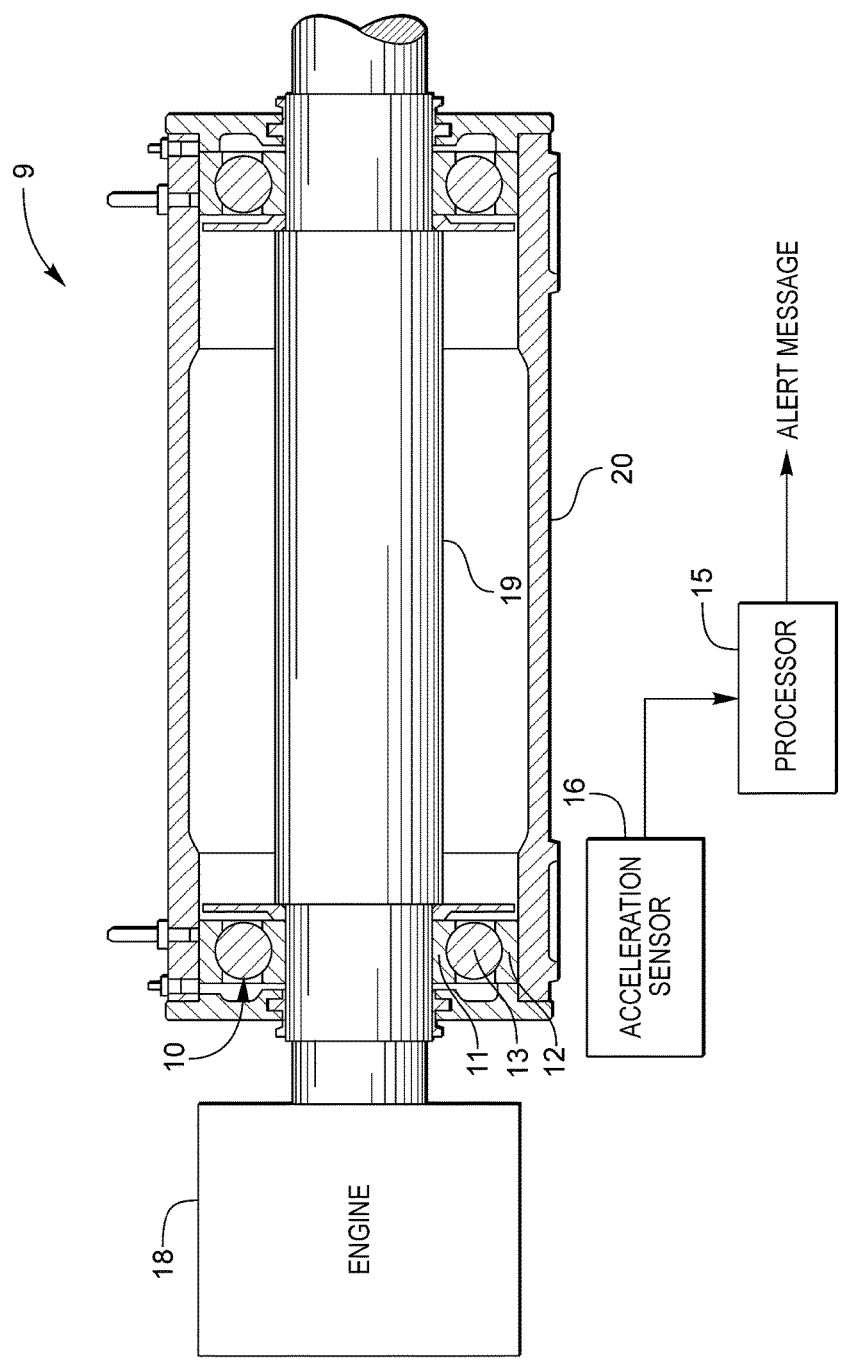
FIG. 7 is a block diagram of a system which implements the method of the invention.

FIG. 7 is a block diagram of a system which implements the method of the invention. System 9 includes an engine 18, a shaft 19, a guide housing 20, bearing 10, an acceleration sensor 16 positioned in a proximity of the bearing, and a processor 15.

An exploded view of one such bearing 10 is shown in FIG. 2. The bearing 10 comprises several components, including an inner ring 11, an outer ring 12, and a plurality of balls 13. It may also have a cage 14 serving to keep the spacing between the balls 13 constant. The balls 13 can roll between the inner and outer rings 11 and 12. Nevertheless, the balls 13 may be replaced by any other type of rolling body, e.g. by cylindrical or conical rollers, or indeed by barrel-shaped rollers.

The bearing 10 is generally part of a device for guiding a component in rotation, such as a shaft transmitting rotary motion and torque. The guide device is itself incorporated in a system 9, such as an engine, having a processor 15 and an acceleration sensor 16.

Firstly, during a preliminary step 1, and during a first substep 101, at least one theoretical fundamental frequency $\alpha^{th}$ is determined for each element 11, 12, and 13 of the bearing 10, said theoretical fundamental frequency $\alpha^{th}$ corresponding to a defect of the element 11, 12, or 13 and depending mainly on the shape of the element 11, 12, or 13 and on its speed of rotation. Nevertheless, there may be a difference between the theoretical fundamental frequency $\alpha^{th}$ and the defect-presence frequency $\hat{\alpha}$. Then during a second substep 102, a frequency dispersion $\Delta f$ around the theoretical fundamental frequency $\alpha^{th}$ is determined together with a theoretical fundamental probability $p^{prior}(f)$ for each frequency f in the range:

$$[\alpha^{th}-\Delta f, \alpha^{th}+\Delta f]$$

genuinely corresponding to that defect of the element 11, 12, or 13. The value of this theoretical fundamental probability $p^{prior}(f)$ lies in the range 0 to 1.

Figure 3:
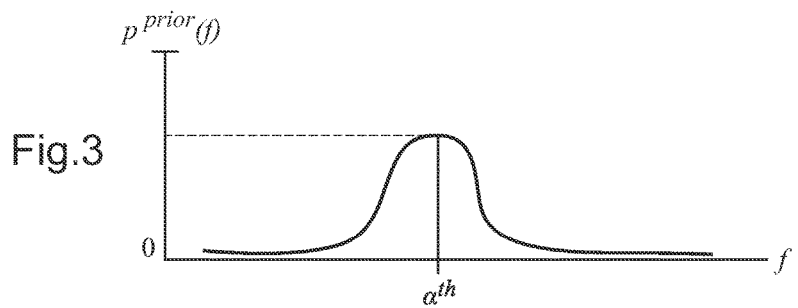
FIG. 3 is a graph plotting a curve representing the theoretical fundamental probability $p^{prior}(f)$ as a function of frequency f.

The frequency dispersion $\Delta f$ and the theoretical fundamental probability $p^{prior}(f)$ may be obtained by experiment, e.g. as a result of measurement performed on bearings having the defect. It is then possible to obtain a curve similar to that shown in FIG. 3, where frequency is plotted along the abscissa axis and the theoretical fundamental probability $p^{prior}(f)$ is plotted up the ordinate axis.

This preliminary step 1 is performed on one occasion only prior to operating the system containing the bearing 10 being monitored by the method of the invention, and unlike the following steps it is not performed at each cycle of the method.

During a preprocessing step 2, in a third substep 201, a time-domain vibration signal $A_n$ is acquired as emitted by an acceleration sensor 16 positioned close to the bearing 10. The time-domain vibration signal $A_n$ is acquired over a predetermined acquisition time and comprises a number of samples N, where n is the order number of each sample in the signal and lies in the range 1 to N. This time-domain vibration signal $A_n$ thus contains information about the vibration emitted by the bearing 10 and more particularly by its elements 11, 12, and 13 and also interfering information that is external to the bearing 10.

By way of example, this predetermined acquisition time may be of the order of about fifty theoretical periods of a vibration signal corresponding to a defect of the bearing 10, where a theoretical period of a vibration signal is the reciprocal of a theoretical fundamental frequency $\alpha^{th}$ of the vibration signal. This acquisition time may represent a duration of the order of three seconds.

During a fourth substep 202 of this preprocessing step 2, the time-domain vibration signal $A_n$ is filtered in order to eliminate the interfering information. This interfering information comprises firstly vibrations emitted by other components of the system in which the bearing 10 forms a part and having vibration frequencies that are generally known, thus making them easily identifiable in the time-domain vibration signal $A_n$, and thus easy to eliminate, and also vibrations that are external to the system and therefore at vibration frequencies that are unknown. In order to eliminate these unknown interfering frequencies, it is important to eliminate the frequencies that are remote from each theoretical fundamental frequency $\alpha^{th}$ and its harmonics. The defect-presence frequency $\hat{\alpha}$ lies in the range:

$$[\alpha^{th} - \Delta f, \alpha^{th} + \Delta f]$$

about each theoretical fundamental frequency $\alpha^{th}$. It is therefore possible to deduce therefrom that any frequency of the time-domain vibration signal $A_n$ that is offset from each of the theoretical fundamental frequencies $\alpha^{th}$ and their harmonics by an amount greater than the associated frequency dispersion $\Delta f$ cannot be a defect-presence frequency $\alpha$, and should therefore be eliminated.

During this fourth substep 202, it is also possible to synchronize the time-domain vibration signal $A_n$ with the speed of rotation of the shaft to which the bearing 10 is connected. The speed of rotation of the shaft may vary during the predetermined acquisition time for the time-domain vibration signal $A_n$, thereby disturbing the time-domain vibration signal $A_n$. However it is possible to correct the time-domain vibration signal $A_n$ by using the instantaneous speed of rotation of the shaft and thus eliminate this disturbance.

After this fourth substep 202 of filtering the time-domain vibration signal $A_n$, a filtered time-domain vibration signal $A'_n$ is obtained that needs to be transformed in order to be analyzed.

For this purpose, during a fifth substep 203, the filtered time-domain vibration signal $A'_n$ is resolved into two signals: a deterministic time-domain vibration signal $D_n$ and a random time-domain vibration signal $E_n$.

By definition, a signal is deterministic if all of its future values are predictable from its past values. It is possible to write such a deterministic time-domain vibration signal $D_n$ in the form:

$$D_n = a_1 \cdot A'_{n-1} + a_2 \cdot A'_{n-2} + \ldots + a_r \cdot A'_{n-r}$$

where $a_1, a_2, \ldots, a_r$ are coefficients that are determined using the known least squares method, i.e. the method involving minimizing the following sum:

$$\Sigma_{n=N-r}^{N}(A'_n - D_n)^2$$

Furthermore, the number r of past samples used for determining this deterministic time-domain vibration signal $D_n$ may be small in order to obtain a compromise between the speed and the accuracy of the deterministic time-domain vibratory calculation. As a result, the number r is less than the number n.

The random time-domain vibration signal $E_n$ is the difference between the filtered time-domain vibration signal $A'_n$ and the deterministic time-domain vibration signal $D_n$, such that:

$$E_n = A'_n - D_n$$

Figure 4:
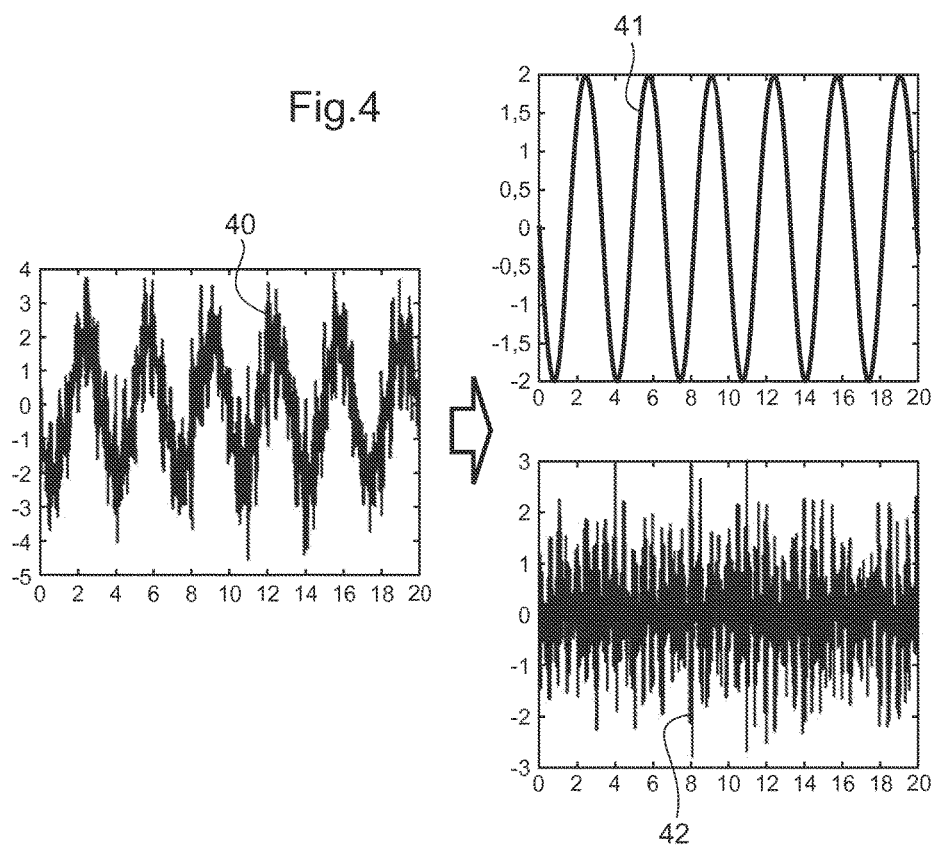

FIG. 4 shows an arbitrary signal 40 being resolved into a deterministic signal 41, which in this particular case is periodic, and a random signal 42. The three graphs in FIG. 4 represent the amplitude of each of the signals as a function of time.

It is then possible to terminate this preprocessing step 2 and make use of the deterministic and random time-domain vibration signals $D_n$ and $E_n$ during analysis step 3.

However, in order to improve the analysis of the vibration signals, it is also possible to improve the impulsiveness of the deterministic and random time-domain vibration signals $D_n$ and $E_n$.

A defect in a bearing 10 gives rise in particular to repeated impacts that lead to peaks of large amplitude in each vibration signal. The presence of high amplitude peaks is a characteristic known as impulsiveness, and it is quantified by an indicator known as the Kurtosis indicator. By amplifying these peaks more particularly, it is possible to reveal the presence of these peaks in the time-domain vibration signal $A_n$. FIG. 5 shows an arbitrary signal 51 in which the impulsiveness has been improved so as to obtain the signal 52. It can be seen that the peaks of the arbitrary signal 51 appear much more clearly in the signal 52. The two graphs of FIG. 5 plot the amplitude of each signal as a function of time.

The deterministic time-domain vibration signal $D_n$ is thus transformed during a sixth substep 204 into an improved deterministic time-domain vibration signal $F_n$, which is a linear combination of earlier samples of the deterministic time-domain vibration signal $D_n$ such that:

$$F_n = b_1 \cdot D_{n-1} + b_2 \cdot D_{n-2} + \ldots + b_p \cdot D_{n-p}$$

where p is the number of samples used for the calculation and where the coefficients $b_1, b_2, \ldots, b_y$ are such that the Kurtosis indicator given by the following formula:

$$\text{Kurtosis}(F_n) = \frac{1}{N} \frac{\sum_{n=1}^{N}\left(F_n - \frac{1}{N}\sum_{n=1}^{N}F_n\right)^4}{\sigma_F^4}$$

is maximized, $\sigma_F$ being the standard deviation of the improved deterministic time-domain vibration signal $F_n$.

The random time-domain vibration signal $E_n$ is transformed during a seventh substep 214 into an improved random time-domain vibration signal $G_n$. An intermediate operation is needed in order to determine an intermediate signal $E'_n$ such that:

$$E'_n = |E_n + i \times H(E_n)|^2$$

where H is the Hilbert transform and i is the imaginary number such that $i^2=-1$. Thereafter, the improved random time-domain vibration signal $G_n$ is determined as a linear combination of earlier sample values of the intermediate signal $E'_n$, as follows:

$$G_n = c_1 \cdot E'_{n-1} + c_2 \cdot E'_{n-2} + \ldots + c_q \cdot E'_{n-q}$$

where q is the number of samples used for the calculation and where the coefficients $c_1, c_2, \ldots c_q$ are such that the Kurtosis indicator given by the formula:

$$\text{Kurtosis}(G_n) = \frac{1}{N} \frac{\sum_{n=1}^{N} \left(G_n - \frac{1}{N}\sum_{n=1}^{N} G_n\right)^4}{\sigma_G^4}$$

is maximized, where $\sigma_G$ is the standard deviation of the improved random time-domain vibration signal $G_n$.

Thus, from the time-domain vibration signal $A_n$ containing interfering information, an improved deterministic time-domain vibration signal $F_n$ and an improved random time-domain vibration signal $G_n$ are obtained that have been filtered and in which frequencies that might represent defects have been amplified. These improved time-domain vibration signals $F_n$ and $G_n$ are thus ready for use during the analysis step 3.

During the analysis step 3, such as performed during a short stoppage period of the rotation of bearing 10, for each element 11, 12, and 13 of the bearing 10 and for the deterministic time-domain vibration signal and the random time-domain vibration signal as obtained at the end of the preprocessing step 2, it is possible to obtain at least one defect-presence frequency $\alpha$ together with an associated reliability level $p(\hat{\alpha})$, with each defect-presence frequency $\hat{\alpha}$ lying in the range:

$$[\alpha^{th} - \Delta f, \alpha^{th} + \Delta f]$$

corresponding to a defect having a theoretical fundamental frequency $\alpha^{th}$.

Thus, each defect-presence frequency $\hat{\alpha}$ and each associated reliability level $p(\hat{\alpha})$ are determined during an eighth substep 301 from the deterministic time-domain vibration signal and during a ninth substep 311 from the random time-domain vibration signal.

In order to determine each defect-presence frequency $\hat{\alpha}$, it is advantageous to process a frequency signal rather than a time-domain signal. Each of the deterministic and random improved time-domain vibration signals is thus transformed respectively into a deterministic frequency-domain vibration signal $J_n$ and a random frequency-domain vibration signal $K_n$ using a known method such as the Fourier transform. Thus, for each frequency-domain vibration signal $J_n$, $K_n$ and for each element 11, 12, 13 of the bearing 10, spectrum lines of amplitude S(f) are obtained. Such a frequency-domain signal is shown in FIG. 6, where the frequency of the signal is plotted along the abscissa axis and its amplitude up the ordinate axis. There can clearly be seen peaks $S_1(f)$, $S_2(f)$, $S_3(f)$, and $S_4(f)$. The first peak $S_1(f)$ is at a frequency that is close to a theoretical fundamental frequency $\alpha^{th}$ in the range:

$$[\alpha^{th} - \Delta f, \alpha^{th} + \Delta f]$$

and it might correspond to the presence of a defect on the corresponding element 11, 12, 13. Likewise, the following peaks $S_2(f)$, $S_3(f)$, and $S_4(f)$ are respectively close to the harmonics $H_1(\alpha^{th})$, $H_2(\alpha^{th})$, and $H_3(\alpha^{th})$ of this theoretical fundamental frequency $\alpha^{th}$.

It is then possible to for each frequency-domain vibration signal $J_n$, $K_n$ and for each frequency f in the range:

$$[\alpha^{th} - \Delta f, \alpha^{th} + \Delta f]$$

to calculate an experimental probability $p^{post}(f)$ for the presence of a defect on each element 11, 12, 13 of the bearing 10.

This experimental probability $p^{post}(f)$ lies in the range 0 to 1 and it may be calculated using the following formula:

$$p^{post}(f) = \frac{p^{prior}(f) \times \prod_{m=1}^{M} S_m(f)}{\int_{v=\alpha^{th}+\Delta f}^{\alpha^{th}+\Delta f} \left[p^{prior}(v) \times \prod_{m=1}^{M} S_m(v)\right] \cdot dv}$$

where $p^{prior}(f)$ is the theoretical fundamental probability of the frequency f in the range:

$$[\alpha^{th} - \Delta f, \alpha^{th} + \Delta f]$$

where $\Delta f$ is the frequency dispersion around the theoretical fundamental frequency $\alpha^{th}$, where $S_m(f)$ is the spectrum line of amplitude for the frequency $m \times f$ such that $S_m(f) = S(m \times f)$, and where M is the number of harmonics of f that are taken into account in the formula.

It is also possible to calculate this experimental probability $p^{post}(f)$ using the following formula:

$$p^{post}(f) = \frac{p^{prior}(f) + \sum_{m=1}^{M} S_m(f)}{\int_{v=\alpha^{th}+\Delta f}^{\alpha^{th}+\Delta f} \left[p^{prior}(v) + \prod_{mn=1}^{M} S_m(v)\right] \cdot dv}$$

or indeed using the following formula:

$$p^{post}(f) = \frac{\min_{m=1 to M} p^{prior}(f) \times S_m(f)}{\int_{v=\alpha^{th}+\Delta f}^{\alpha^{th}+\Delta f} \min_{m=1 to M} \left[p^{prior}(v) \times S_m(v)\right] \cdot dv}$$

It is then possible, for each element 11, 12, 13, and for each frequency-domain vibration signal $J_n$, $K_n$ to determine each defect-presence frequency $\hat{\alpha}$ for which the experimental probability $p^{post}(f)$ is at a maximum when f passes through the range:

$$[\alpha^{th} - \Delta f, \alpha^{th} + \Delta f]$$

each associated reliability level $p(\hat{\alpha})$ being equal to this maximum experimental probability $p^{post}(f)$.

Finally, during diagnosis step 4, which comprises a single tenth substep 401, an alert message is possibly issued indicating at least one defect on at least one element 11, 12, 13 of the bearing 10 as a function of the values of each defect-presence frequency $\hat{\alpha}$ and each associated reliability level $p(\hat{\alpha})$.

Advantageously, this alert message serves to identify the defect that has been detected and the corresponding element 11, 12, 13, since each defect-presence frequency $\hat{\alpha}$ is specific to a given defect and to a particular element 11, 12, 13 of the bearing 10.

For example, if two defect-presence frequencies $\hat{\alpha}$ in the deterministic time-domain vibration signal $D_n$ and in the random time-domain vibration signal $E_n$ are far apart, then at least three situations can be distinguished:

either at least one of the two defect-presence frequencies $\hat{\alpha}$ has a reliability level $p(\hat{\alpha})$ that is small compared with the other, so account is taken only of the defect-presence frequency $\hat{\alpha}$ having a high level of reliability $p(\hat{\alpha})$ and of this high level of reliability $p(\hat{\alpha})$ in order to trigger an alert message, where appropriate;

or both defect-presence frequencies $\hat{\alpha}$ have high levels of reliability $p(\hat{\alpha})$ so an alert message is possibly triggered depending on the maintenance strategy that has been decided by the user, for example by combining the two reliability levels $p(\hat{\alpha})$;

or else both of the reliability levels $p(\hat{\alpha})$ are low and no alert message is triggered.

Otherwise, when the two defect-presence frequencies $\hat{\alpha}$ are close together, the two reliability levels $p(\hat{\alpha})$ are combined.

Under all circumstances, the single reliability level $p(\hat{\alpha})$ that is used or the combination of the two reliability levels $p(\hat{\alpha})$ is compared with an alert threshold and if the alert threshold is exceeded an alert message is issued corresponding to the presence of a defect on the element 11, 12, 13 under consideration.

The alert thresholds for each element 11, 12, 13 are determined by the person skilled in the art as a function of a large number of reference states for a bearing 10 that is sound or degraded.

Naturally, the present invention may be subjected to numerous variations as to its implementation. Although several implementations are described, it will readily be understood that it is not conceivable to identify exhaustively all possible implementations. It is naturally possible to envisage replacing any of the means described by equivalent means without going beyond the ambit of the present invention.

What is claimed is:

1. A system comprising:
   an engine;
   a rotary shaft connected to the engine;
   wherein the engine is configured to transmit rotary motion and torque via the shaft;
   a guide housing that is stationary;
   a rolling bearing providing rotary support to the shaft, the bearing including an inner ring fixed to the shaft to rotate therewith, an outer ring fixed to the guide housing to be fixed stationary, and a plurality of rolling bodies rolling between the inner ring and the outer ring as the shaft rotates;
   an acceleration sensor positioned in a proximity of the bearing, the acceleration sensor configured to detect vibration emitted from the proximity of the bearing including vibration emitted by the bearing while the shaft is rotating and to generate a time-domain vibration signal $A_n$ indicative of the emitted vibration detected by the acceleration sensor; and
   a processor responsible for detecting defects in the bearing;
   the processor configured to, during a preliminary stage prior to the shaft being rotated by the engine,
      determine, for each element of the bearing, at least one theoretical fundamental frequency $\alpha^{th}$ corresponding to a defect of the element; and
      for the defect of the element determine a frequency dispersion $\Delta f$ serving to define a range:

$[\alpha^{th}-\Delta f, \alpha^{th}+\Delta f]$ around the theoretical fundamental frequency $\alpha^{th}$;
   the processor further configured to, during a preprocessing stage while the shaft is being rotated by the engine at a speed of rotation that is stable,
      acquire from the acceleration sensor while the shaft is rotating the time-domain vibration signal $A_n$ indicative of the emitted vibration detected by the acceleration sensor, the time-domain vibration signal $A_n$ including a number N of samples over a predetermined acquisition time, where n is the order number of each sample and lies in the range 1 to N; and
      transform the time-domain vibration signal $A_n$ for analysis;
   the processor further configured to, during an analysis stage while the shaft is being rotated by the engine at the speed of rotation that is stable,
      determine for each element of the bearing at least one defect-presence frequency $\hat{\alpha}$ in the element together with an associated reliability level $p(\hat{\alpha})$ at each defect-presence frequency $\hat{\alpha}$, the defect-presence frequency $\hat{\alpha}$ corresponding to a vibration frequency characteristic of a defect present in an element of the bearing and lying in the range:

$[\alpha^{th}-\Delta f, \alpha^{th}+\Delta f]$ corresponding to the detected defect, the reliability level $p(\hat{\alpha})$ being a probability of a defect $\hat{\alpha}$ being present in an element of the bearing; and
   the processor further configured to, during a diagnosis stage while the shaft is being rotated by the engine at the speed of rotation that is stable,
      deliver an alert message, indicating at least one defect in at least one element of the bearing as a function of the values of each defect-presence frequency $\hat{\alpha}$ and of each associated reliability level $p(\hat{\alpha})$, to act on the system prior to the speed of rotation of the shaft varying.

2. The system of claim 1, wherein:
   the processor is further configured to
      filter the time-domain vibration signal $A_n$ to obtain a filtered time-domain vibration signal $A'_n$; and
      transform the filtered time-domain vibration signal $A'_n$ to obtain a deterministic time-domain vibration signal and a random time-domain vibration signal.

3. The system of claim 2, further comprising:
   an instantaneous speed sensor for measuring an instantaneous speed of rotation of the shaft; and
   wherein the processor is further configured to filter the time-domain vibration signal $A_n$ to obtain the filtered time-domain vibration signal $A'_n$ by synchronizing the time-domain vibration signal $A_n$ with the instantaneous speed of rotation of the shaft as measured by the instantaneous speed sensor.

4. The system of claim 2, wherein:
   the processor is further configured to filter the time-domain vibration signal $A_n$ to obtain the filtered time-domain vibration signal $A'_n$ by eliminating interfering vibratory components present in the time-domain vibration signal $A_n$.

5. The system of claim 4, wherein:
   the processor is further configured to
      transform the time-domain vibration signal $A_n$ into a frequency-domain vibration signal $B_n$;
      eliminate from the frequency-domain vibration signal $B_n$ vibration frequencies that come from the shaft while the shaft is rotating, wherein vibration frequencies of the shaft while the shaft is rotating are known;

eliminate from the frequency-domain vibration signal $B_n$ vibration frequencies that are offset from each theoretical fundamental frequency $\alpha^{th}$ of each element of the bearing and its harmonics by an amount that is greater than the frequency dispersion $\Delta f$ corresponding to each theoretical fundamental frequency $\alpha^{th}$; and transform the frequency-domain vibration signal $B_n$ as modified in this way to obtain a time-domain vibration signal.

6. The system of claim 2, wherein:
the processor is further configured to resolve the filtered time-domain vibration signal $A'_n$ into two signals:
(i) a deterministic time-domain vibration signal $D_n$, which is a linear combination of past values of the filtered time-domain vibration signal $A'_n$, such that:

$$D_n = a_1 \cdot A'_{n-1} + a_2 \cdot A'_{n-2} + \ldots + a_r \cdot A'_{n-r}$$

where $a_1, a_2, \ldots, a_r$ are coefficients determined in such a manner that the sum:

$$\Sigma_{m=N-r}^{N}(A'_n - D_n)^2$$

is minimized and where r is the number of samples used for calculating the deterministic signal and is less than n; and (ii) a random time-domain vibration signal $E_n$, which is the difference between the filtered time-domain vibration signal $A'_n$ and the deterministic time-domain vibration signal $D_n$.

7. The system of claim 6, wherein:
the processor is further configured to improve the impulsivity of the deterministic time-domain vibration signal $D_n$ to obtain an improved deterministic time-domain vibration signal $F_n$, which is a linear combination of earlier samples of the deterministic time-domain vibration signal $D_n$ such that:

$$F_n = b_1 \cdot D_{n-1} + b_2 \cdot D_{n-2} + \ldots + b_p \cdot D_{n-p}$$

where the coefficients $b_1, b_2, \ldots, b_p$ are determined so that the Kurtosis indicator given by the following formula:

$$\mathrm{Kurtosis}(F_n) = \frac{1}{N} \frac{\sum_{n=1}^{N}\left(F_n - \frac{1}{N}\sum_{n=1}^{N} F_n\right)^4}{\sigma_F^4}$$

is maximized, where $\sigma_F$ is the standard deviation of the improved deterministic time-domain vibration signal $F_n$, where p is the number of samples used for calculating the improved deterministic time-domain vibration signal $F_n$ and is less than n, and where the improved deterministic time-domain vibration signal $F_n$ is then suitable for use in the analysis stage.

8. The system of claim 6, wherein:
the processor is further configured to improve the impulsivity of the random time-domain vibration signal $E_n$ to obtain an improved random time-domain vibration signal $G_n$ by initially transforming the random time-domain vibration signal $E_n$ to obtain an intermediate signal $E'_n$ such that:

$$E'_n = |E_n + i \times H(E_n)|^2$$

where H is the Hilbert transform and i is the imaginary number such that $i^2 = -1$, and then subsequently determining the improved random time-domain vibration signal $G_n$, which is a linear combination of earlier samples of the intermediate signal $E'_n$ such that:

$$G_n = c_1 \cdot E'_{n-1} + c_2 \cdot E'_{n-2} + \ldots + c_q \cdot E'_{n-q}$$

where the coefficients $c_1, c_2, \ldots, c_q$ are determined so that the Kurtosis indicator given by the following formula:

$$\mathrm{Kurtosis}(G_n) = \frac{1}{N} \frac{\sum_{n=1}^{N}\left(G_n - \frac{1}{N}\sum_{n=1}^{N} G_n\right)^4}{\sigma_G^4}$$

is maximized, where $\sigma_G$ is the standard deviation of the improved random time-domain vibration signal $G_n$, where q is the number of samples used for calculating the improved deterministic time-domain vibration signal $G_n$ and is less than n, and where the improved random time-domain vibration signal $G_n$ can then be used during the analysis stage.

9. The system of claim 2, wherein:
the processor is further configured to, during the analysis stage
transform the deterministic time-domain vibration signal and the random time-domain vibration signal respectively into a deterministic frequency-domain vibration signal $J_n$ and a random frequency-domain vibration signal $K_n$ to obtain spectrum lines of amplitude S(f) for each frequency-domain vibration signal $J_n$, $K_n$ and for each element;
calculate for each frequency-domain vibration signal $J_n$, $K_n$ and for each frequency f in the range:

$$[\alpha^{th} - \Delta f, \alpha^{th} + \Delta f]$$

an experimental probability $p^{post}(f)$ for the presence of a defect in each element of the bearing; and
determine for each element of the bearing and for each frequency-domain vibration signal $J_n$, $K_n$ firstly the defect-presence frequency $\hat{\alpha}$ corresponding to a maximum experimental probability $p^{post}(f)$ when f passes through the range:

$$[\alpha^{th} - \Delta f, \alpha^{th} + \Delta f]$$

and secondly the associated reliability level $p(\hat{\alpha})$, which is equal to the maximum experimental probability $p^{post}(f)$.

10. The system of claim 9, wherein for a theoretical fundamental probability $p^{prior}(f)$ that each frequency f in the range:

$$[\alpha^{th} - \Delta f, \alpha^{th} + \Delta f]$$

corresponds to the defect in the element of the bearing being determined during the preliminary stage, the processor is further configured to calculate the experimental probability $p^{post}(f)$ using the following formula:

$$p^{post}(f) = \frac{p^{prior}(f) \times \prod_{m=1}^{M} S_m(f)}{\int_{v=\alpha^{th} + \Delta f}^{\alpha^{th} + \Delta f} \left[p^{prior}(v) \times \prod_{m=1}^{M} S_m(v)\right] \cdot dv}$$

where $\Delta f$ is the frequency dispersion about the theoretical fundamental frequency $\alpha^{th}$, where $S_m(f)$ is the amplitude of the spectrum line for the frequency m×f such that $S_m(f)=S(m\times f)$, where f lies in the range:

$$[\alpha^{th}-\Delta f, \alpha^{th}+\Delta f]$$

and where M is the number of harmonics of f considered in the formula.

11. The system of claim 9, wherein for a theoretical fundamental probability $p^{prior}(f)$ that each frequency f in the range:

$$[\alpha^{th}-\Delta f, \alpha^{th}+\Delta f]$$

corresponds to the defect in the element of the bearing being determined during the preliminary stage, the processor is further configured to calculate the experimental probability $p^{post}(f)$ using the following formula:

$$p^{post}(f) = \frac{p^{prior}(f) + \sum_{m=1}^{M} S_m(f)}{\int_{v=\alpha^{th}+\Delta f}^{\alpha^{th}+\Delta f} \left[ p^{prior}(v) + \sum_{m=1}^{M} S_m(v) \right] \cdot dv}$$

where $\Delta f$ is the frequency dispersion about the theoretical fundamental frequency $\alpha^{th}$, where $S_m(f)$ is the amplitude of the spectrum line for the frequency m×f such that $S_m(f)=S(m\times f)$, where f lies in the range:

$$[\alpha^{th}-\Delta f, \alpha^{th}+\Delta f]$$

and where M is the number of harmonics of f considered in the formula.

12. The system of claim 9, wherein for a theoretical fundamental probability $p^{prior}(f)$ that each frequency f in the range:

$$[\alpha^{th}-\Delta f, \alpha^{th}+\Delta f]$$

corresponds to the defect in the element of the bearing being determined during the preliminary stage, the processor is further configured to calculate the experimental probability $p^{post}(f)$ using the following formula:

$$p^{post}(f) = \frac{\min_{m=1\,to\,M} p^{prior}(f) \times S_m(f)}{\int_{v=\alpha^{th}+\Delta f}^{\alpha^{th}+\Delta f} \min_{m=1\,to\,M} [p^{prior}(v) \times S_m(v)] \cdot dv}$$

where $\Delta f$ is the frequency dispersion about the theoretical fundamental frequency $\alpha^{th}$, where $S_m(f)$ is the amplitude of the spectrum line for the frequency m×f such that $S_m(f)=S(m\times f)$, where f lies in the range:

$$[\alpha^{th}-\Delta f, \alpha^{th}+\Delta f]$$

and where M is the number of harmonics of f considered in the formula.

13. The system of claim 1, wherein:
during the diagnosis stage, when, for the defect in the element of the bearing, the experimental defect frequencies $\hat{\alpha}$ are far apart from one another, the processor is further configured to
when the respective reliability levels $p(\hat{\alpha})$ are large, combine the values of each of the reliability levels $p(\hat{\alpha})$ using a first predetermined relationship and deliver an alert message indicating the defect if the result of the combination is greater than a predetermined alert threshold; and
when a reliability level $p(\hat{\alpha})$ of one of the two experimental defect frequencies $\hat{\alpha}$ is small compared with the other, deliver an alert message indicating the defect solely for the defect-presence frequency $\hat{\alpha}$ as a function of the associated reliability level $p(\hat{\alpha})$.

14. The system of claim 1, wherein, during a diagnosis stage, the processor is further configured to when for the defect in the element of the bearing the experimental defect frequencies $\hat{\alpha}$ are close together, combine the values of each reliability level $p(\hat{\alpha})$ using a second predetermined relationship and deliver an alert message indicating the defect if the result of the combination is greater than a predetermined alert threshold.

15. The system of claim 1, wherein the predetermined acquisition time for acquiring the time-domain vibration signal $A_n$ is of the order of fifty periods $T^{th}$ of a vibration signal corresponding to a defect in the bearing, where the period $T^{th}$ is the reciprocal of the theoretical fundamental frequency $\alpha^{th}$, such that $T^{th}=1/\alpha^{th}$.

16. The system of claim 1, wherein the predetermined acquisition time for acquiring the time-domain vibration signal $A_n$ is of the order of three seconds.

17. The system of claim 1, wherein the processor is further configured to transform a time-domain vibration signal into a frequency-domain signal by applying the Fourier transform.

18. The system of claim 1, further comprising:
an instantaneous speed sensor for measuring an instantaneous speed of rotation of the shaft; and
wherein the processor is further configured to, during the preprocessing stage while the shaft is being rotated by the engine, synchronize the time-domain vibration signal $A_n$ with the instantaneous speed of rotation of the shaft as measured by the instantaneous speed sensor to eliminate a disturbance in the time-domain vibration signal $A_n$ caused by variance in the instantaneous speed of rotation of the shaft.

19. A method for use with a system having an engine, a rotary shaft connected to the engine, a guide housing that is stationary, and a rolling bearing providing rotary support to the shaft, the bearing including an inner ring fixed to the shaft to rotate therewith, an outer ring fixed to the guide housing to be fixed stationary, and a plurality of rolling bodies rolling between the inner ring and the outer ring as the shaft rotates, wherein the engine is configured to transmit rotary motion and torque via the shaft, the method comprising:
during a preliminary step prior to the shaft being rotated being rotated by the engine,
determining, by a processor, for each element of the bearing, at least one theoretical fundamental frequency $\alpha^{th}$ corresponding to a defect of the element; and
for the defect of the element determining, by the processor, a frequency dispersion $\Delta f$ serving to define a range:

$$[\alpha^{th}-\Delta f, \alpha^{th}+\Delta f]$$

around the theoretical fundamental frequency $\alpha^{th}$;
operating the engine to transmit rotary motion and torque via the shaft;
during a preprocessing step while the shaft is being rotated by the engine at a speed of rotation that is stable,
detecting, by an acceleration sensor positioned in a proximity of the bearing, vibration emitted from the proximity of the bearing including vibration emitted by the bearing while the shaft is rotating and generating, by the acceleration sensor, a time-domain vibration signal $A_n$ indicative of the emitted vibration detected by the acceleration sensor;

acquiring from the acceleration sensor, by the processor, while the shaft is rotating the time-domain vibration signal $A_n$ indicative of the emitted vibration detected by the acceleration sensor, the time-domain vibration signal $A_n$ including a number N of samples over a predetermined acquisition time, where n is the order number of each sample and lies in the range 1 to N; and transforming, by the processor, the time-domain vibration signal $A_n$ for analysis;

during an analysis step while the shaft is being rotated by the engine at the speed of rotation that is stable, determining, by the processor, for each element of the bearing at least one defect-presence frequency $\hat{\alpha}$ in the element together with an associated reliability level $p(\hat{\alpha})$ at each defect-presence frequency $\hat{\alpha}$, the defect-presence frequency $\hat{\alpha}$ corresponding to a vibration frequency characteristic of a defect present in an element of the bearing and lying in the range:

$$[\alpha^{th}-\Delta f, \alpha^{th}+\Delta f]$$

corresponding to the detected defect, the reliability level $p(\hat{\alpha})$ being a probability of a defect $\hat{\alpha}$ being present in an element of the bearing;

during a diagnosis step while the shaft is being rotated by the engine at the speed of rotation that is stable, delivering, by the processor, an alert message indicating at least one defect in at least one element of the bearing as a function of the values of each defect-presence frequency $\hat{\alpha}$ and of each associated reliability level $p(\hat{\alpha})$; and acting on the system in response to the alert message while the shaft is being rotated by the engine at the speed of rotation that is stable to take action prior to the speed of rotation of the shaft varying.

20. The method of claim 19, further comprising:

during the preprocessing step while the shaft is being rotated by the engine, detecting, by an instantaneous speed sensor, an instantaneous speed of rotation of the shaft;

synchronizing, by the processor, the time-domain vibration signal $A_n$ with the instantaneous speed of rotation of the shaft as measured by the instantaneous speed sensor to eliminate a disturbance in the time-domain vibration signal $A_n$ caused by variance in the instantaneous speed of rotation of the shaft.

* * * * *